(12) United States Patent
Howard

(10) Patent No.: US 9,403,008 B2
(45) Date of Patent: Aug. 2, 2016

(54) MANAGING BACK PAIN BY APPLYING A HIGH FREQUENCY ELECTRICAL STIMULUS DIRECTLY TO THE SPINAL CORD

(71) Applicant: University of Iowa Research Foundation, Iowa City, IA (US)

(72) Inventor: Matthew A. Howard, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 8 days.

(21) Appl. No.: 14/375,785

(22) PCT Filed: Jan. 30, 2013

(86) PCT No.: PCT/US2013/023897
§ 371 (c)(1),
(2) Date: Jul. 30, 2014

(87) PCT Pub. No.: WO2013/116368
PCT Pub. Date: Aug. 8, 2013

(65) Prior Publication Data
US 2014/0379043 A1    Dec. 25, 2014

Related U.S. Application Data

(60) Provisional application No. 61/592,520, filed on Jan. 30, 2012.

(51) Int. Cl.
*A61N 1/32* (2006.01)
*A61N 1/34* (2006.01)
(Continued)

(52) U.S. Cl.
CPC .......... *A61N 1/36071* (2013.01); *A61N 1/0553* (2013.01); *A61N 1/0558* (2013.01);
(Continued)

(58) Field of Classification Search
None
See application file for complete search history.

(56) References Cited

U.S. PATENT DOCUMENTS

| 3,612,061 | A | 10/1971 | Collins et al. |
| 3,724,467 | A | 4/1973 | Avery et al. |

(Continued)

FOREIGN PATENT DOCUMENTS

| CN | 101048194 A | 10/2007 |
| EP | 1 048 317 A2 | 11/2000 |

(Continued)

OTHER PUBLICATIONS

International Search Report and Written Opinion for PCT Application No. PCT/US2011/060462 mailed Mar. 2, 2012.

(Continued)

*Primary Examiner* — Carl H Layno
*Assistant Examiner* — Jon Eric C Morales
(74) *Attorney, Agent, or Firm* — Kilpatrick Townsend and Stockton LLP

(57) ABSTRACT

This invention provides a new technology for management of back pain by stimulating the spinal cord in a manner that renders it refractory to transmission of deleterious or undesirable sensory input. The electrical stimulus comprises high frequency pulses in a regular or complex pattern or that are stochastically produced under microprocessor control. The stimulus is applied directly to the surface of the spinal cord from within the spinal canal, which provides important benefits over previous technology. The stimulus alleviates symptoms and signs of back pain, while minimizing the risk of side effects such as paresthesia, and potentially minimizing the effects on motor neuron transmission and proprioception.

23 Claims, 11 Drawing Sheets

(51) Int. Cl.
*A61N 1/36* (2006.01)
*A61N 1/05* (2006.01)
*A61N 1/06* (2006.01)
*A61N 1/372* (2006.01)

(52) U.S. Cl.
CPC .............. *A61N 1/06* (2013.01); *A61N 1/36067* (2013.01); *A61N 1/36103* (2013.01); *A61N 1/36114* (2013.01); *A61N 1/36139* (2013.01); *A61N 1/36171* (2013.01); *A61N 1/37223* (2013.01)

(56) References Cited

U.S. PATENT DOCUMENTS

| | | | |
|---|---|---|---|
| 3,822,708 | A | 7/1974 | Zilber |
| 4,549,556 | A | 10/1985 | Tarjan et al. |
| 4,590,946 | A | 5/1986 | Loeb |
| 4,837,049 | A | 6/1989 | Byers et al. |
| 6,175,769 | B1 | 1/2001 | Errico et al. |
| 6,295,472 | B1 | 9/2001 | Rubinstein et al. |
| 6,319,241 | B1* | 11/2001 | King et al. ............ 604/502 |
| 6,549,810 | B1 | 4/2003 | Leonard et al. |
| 6,631,295 | B2 | 10/2003 | Rubinstein et al. |
| 7,333,857 | B2 | 2/2008 | Campbell |
| 7,337,006 | B2 | 2/2008 | Kim et al. |
| 7,769,472 | B2 | 8/2010 | Gerber |
| 8,170,675 | B2 | 5/2012 | Alataris et al. |
| 8,209,021 | B2 | 6/2012 | Alataris et al. |
| 8,255,057 | B2 | 8/2012 | Fang et al. |
| 8,295,945 | B1 | 10/2012 | Thacker et al. |
| 8,649,874 | B2 | 2/2014 | Alataris et al. |
| 8,712,533 | B2 | 4/2014 | Alataris et al. |
| 8,838,248 | B2 | 9/2014 | Walker et al. |
| 8,892,209 | B2 | 11/2014 | Alataris et al. |
| 2002/0111660 | A1 | 8/2002 | Errico et al. |
| 2003/0204228 | A1 | 10/2003 | Cross et al. |
| 2004/0162594 | A1* | 8/2004 | King ............... A61N 1/36007 607/40 |
| 2004/0176831 | A1 | 9/2004 | Gliner et al. |
| 2005/0131506 | A1 | 6/2005 | Rezai et al. |
| 2007/0073357 | A1 | 3/2007 | Rooney et al. |
| 2008/0234791 | A1 | 9/2008 | Arle et al. |
| 2009/0281599 | A1 | 11/2009 | Thacker et al. |
| 2010/0057177 | A1 | 3/2010 | Moffitt et al. |
| 2010/0057178 | A1* | 3/2010 | Simon ..................... 607/117 |
| 2010/0063568 | A1 | 3/2010 | Staunton et al. |
| 2010/0100165 | A1 | 4/2010 | Swanson et al. |
| 2010/0145428 | A1 | 6/2010 | Cameron et al. |
| 2010/0204766 | A1 | 8/2010 | Zdeblick et al. |
| 2011/0184488 | A1 | 7/2011 | De Ridder |
| 2011/0224755 | A1 | 9/2011 | Arle et al. |
| 2012/0016438 | A1 | 1/2012 | Alataris et al. |
| 2014/0128955 | A1* | 5/2014 | Howard et al. ............. 607/117 |
| 2014/0371830 | A1 | 12/2014 | Howard et al. |
| 2015/0005680 | A1* | 1/2015 | Lipani ..................... 601/15 |

FOREIGN PATENT DOCUMENTS

| | | |
|---|---|---|
| WO | 95/32677 A1 | 12/1995 |
| WO | 2006/029257 A2 | 3/2006 |
| WO | 2010/124139 A1 | 10/2010 |
| WO | 2012/065125 A1 | 5/2012 |
| WO | 2013/116377 A1 | 8/2013 |

OTHER PUBLICATIONS

International Search Report and Written Opinion for PCT Application No. PCT/US2013/023912 mailed Jun. 4, 2013.

International Search Report and Written Opinion for PCT Application No. PCT/US2013/023897 mailed Apr. 16, 2013.

Eldabe et al., "An Analysis of the Components of Pain, Function, and Health-Related Quality of Life in Patients with Failed Back Surgery Syndrome Treated with Spinal Cord Stimulation or Conventional Medical Management," Neuromodulation 13(3): 201-209 (2010).

Gibson-Corley et al., "Ovine Tests of a Novel Spinal Cord Neuromodulator and Dentate Ligament Fixation Method," Journal of Investigative Surgery 25(6): 366-374 (2012).

Gibson-Corley et al., "Postsurgical Pathologies Associated with Intradural Electrical Stimulation in the Central Nervous System: Design Implications for a New Clinical Device," BioMed Research International 2014, Article ID No. 989175 (2014).

"Nevro Corp. Announces Publication of Positive Six-Month Clinical Data for Senza HF10 High-Frequency Spinal Cord Stimulation Therapy in Europe," Nevro Newsroom Press Release dated Feb. 6, 2013, downloaded from http://www.nevro.com/nevro-corp-announces-publication-of-positive-six-month-clinical-data-for-senza-hf10-high-frequency-spinal-cord-stimulation-therapy-in-europe/ on Aug. 6, 2014.

Oliynyk et al., "Dynamic Loading Characteristics of an Intradural Spinal Cord Stimulator," Journal of Applied Physics 113: 026103 (2013).

Oya et al., "Soft-Coupling Suspension System for an Intradural Spinal Cord Stimulator: Biophysical Performance Characteristics," Journal of Applied Physics 114: 164701 (2013).

Viljoen et al., "MR-Based Measurement of Spinal Cord Motion During Flexion of the Spine: Implications for Intradural Spinal Cord Stimulator Systems," Journal of Medical Engineering and Technology 38(1): 1-4 (2014).

Wilson et al., "Pulsatile Spinal Cord Surrogate for Intradural Neuromodulation Studies," Journal of Medical Engineering and Technology 36(1): 22-25 (2012).

Extended European Search Report for EP Application No. 11839545.8 mailed Apr. 24, 2014.

International Search Report and Written Opinion of the International Searching Authority mailed on Dec. 23, 2014 for PCT Patent Application No. PCT/US2014/054243, 13 pages.

Sweet, W.H. et al. (1974). "Stimulation of the Posterior Columns of the Spinal Cord for Pain Control: Indications, Technique, and Results," *Clinical Neurosurgery* 21:278-310.

Burton, "Safety and Clinical Efficacy of Implanted Neuroaugmentive Spinal Devices for the Relief of Pain", Appl. Neurophysiol. 1977-78; 40:175-83.

Flouty et al., "A new device concept for directly modulating spinal cord pathways: initial in vivo experimental results", Physiol Meas. Dec. 2012;33(12):2003-15.

Flouty et al., "Intracranial Somatosensory Responses with Direct Spinal Cord Stimulation in Anesthetized Sheep", PLOS ONE, Feb. 2013, vol. 8, e56266, pp. 1-11.

Gibson-Corley et al., "Ovine tests of a novel spinal cord neuromodulator and dentate ligament fixation method", J Invest Surg. Dec. 2012;25(6):366-74.

Gibson-Corley et al., "Postsurgical Pathologies Associated with Intradural Electrical Stimulation in the Central Nervous System: Design Implications for a New Clinical Device", BioMed Research International, vol. 2014, Article ID 989175, 10 pages.

Gildenberg PL, "Evolution of Spinal Cord Surgery for Pain", Clinical Neurosurgery, 2006; 53:11-7.

Howell et al., "Evaluation of Intradural Stimulation Efficiency and Selectivity in a Computational Model of Spinal Cord Stimulation", PLoS ONE 9(12): e114938, 1-25.

Huang et al., "Comparison of spinal cord stimulation profiles from intra- and extradural electrode arrangements by finite element modeling", Med Biol Eng Comput (2014) 52:531-538.

Long, "Electrical Stimulation for the Control of Pain", Symposium on Pain, Arch Surg., Jul. 1977; 112(7), 884-8.

Long, "The Current Status of Electrical Stimulation of the Nervous System for the Relief of Chronic Pain", Surg Neurol, Feb. 1998; 49(2); 142-4.

Mayfield Clinic & Spine Institute, "Spinal Cord Stimulation, advanced level", accessible on www.mayfieldclinic.com, 2002, 6 pages.

Oya et al., "Applier tool for intradural spinal cord implants", J Med Eng Technol. Apr. 2012;36(3):169-73.

Oya et al., "Spinal canal surrogate for testing intradural implants", J Med Eng Technol. Nov. 2012;36(8):407-10.

(56) References Cited

OTHER PUBLICATIONS

Safayi et al., "Biomechanical performance of an ovine model of intradural spinal cord stimulation", J Med Eng Technol. Jul. 2014;38(5):269-73.
Shealy et al., "Dorsal Column Electroanalgesia", J. Neurosurg., May 1970;32(5), 560-4.
Song et al., "Power and signal transmission protocol for a contactless subdural spinal cord stimulation device", Biomed Microdevices. Feb. 2013;15(1):27-36.
Viljoen et al., "Apparatus for simulating dynamic interactions between the spinal cord and soft-coupled intradural implants", Rev Sci Instrum. Nov. 2013;84(11):114303.
Viljoen et al., "MR-based measurement of spinal cord motion during flexion of the spine: implications for intradural spinal cord stimulator systems", J Med Eng Technol. Jan. 2014;38(1):1-4.
Wilson et al., "Pulsatile spinal cord surrogate for intradural neuromodulation studies", J Med Eng Technol. Jan. 2012;36(1):22-5.
About Nevro website: http://www.nevro.com/about-us/who-we-are/, accessed on Sep. 22, 2015, 1 page.
Holsheimer et al., "Computer modelling of spinal cord stimulation and its contribution to therapeutic efficacy", Spinal Cord (1998), 36, pp. 531-540.
Holsheimer et al., "Effects of Electrode Positioning on Perception Threshold and Paresthesia Coverage in Spinal Cord Stimulation", Neuromodulation: Technology at the Neural Interface, vol. 10, No. 1, 2007, pp. 34-41.
Holsheimer et al., "Optimum electrode geometry for spinal cord stimulation: the narrow bipole and tripole", Medical & Biological Engineering & Computing, Sep. 1997, pp. 493-497.
Holsheimer et al., "Spinal Geometry and Paresthesia Coverage in Spinal Cord Stimulation", Neuromodulation, vol. 1, No. 3, 1998, pp. 129-136.
Holsheimer et al., "Which Neuronal Elements are Activated Directly by Spinal Cord Stimulation", Neuromodulation, vol. 5, No. 1, 2002, pp. 25-31.
Nevro pamphlet, "High-Frequency Spinal Cord Stimulation", 2012004 Rev. D, 4 pages.
Supplementary EP Search Report mailed on Sep. 25, 2015 for EP Application No. 13743674.7, 5 pages.

\* cited by examiner

MANAGING BACK PAIN BY APPLYING A HIGH FREQUENCY ELECTRICAL STIMULUS DIRECTLY TO THE SPINAL CORD

REFERENCE TO RELATED APPLICATIONS

This application is the U.S. National Stage of International Application PCT/US2013/023897, filed Jan. 30, 2013, which was published as WO 2013/116368 on Aug. 8, 2013. This application claims the priority benefit of U.S. provisional application 61/592,520 filed Jan. 30, 2012. The priority application and published PCT application WO 2012/065125 are hereby incorporated herein by reference in their entirety for all purposes.

FIELD OF THE INVENTION

The invention relates generally to the field of medical devices and pain management. In particular, it relates to structures, electrode arrays and electronics for applying high frequency electrical stimulation to the spinal cord

BACKGROUND

Chronic pain is an often unbearable sequelae of spinal cord injury or disease. It can interfere with the basic activities, effective rehabilitation, and quality of life of the patient. Pain in the cord-injured patient is often recalcitrant to treatment. This problem is amplified by the limited availability of effective pharmacological and nonpharmacological treatment options.

The prevalence of pain in patients with spinal cord injury is high: in some studies ranging from about 62% to 84% of patients. Back pain is also a feature of other injuries and conditions. For example, postural abnormalities and increased muscle tone in Parkinson's disease may cause back pain, were the prevalence can be as high as 74%. Other conditions associated with back pain include congestive heart failure and osteoarthritis.

Because back pain is often intractable within the current spectrum of clinical modalities, there is a need for new technology designed for pain management.

SUMMARY OF THE INVENTION

This invention provides a new technology for applying a stimulus directly to the surface of the spinal cord from within the spinal canal. The stimulus alleviates symptoms and signs of back pain, while minimizing the risk of side effects such as paresthesia.

One aspect of the invention is a method, a device, and a system for stimulating a spinal cord of a subject who is prone to deleterious nerve signals transmitted along the spinal cord. The method comprises implanting an electrode array within the spinal canal of the subject so that the electrodes engage the spinal cord; and then applying an electrical stimulus through the electrodes in the array directly to the spinal cord so that the electrical stimulus inhibits transmission of the deleterious nerve signals along the spinal cord. The electrical stimulus has a sufficiently high frequency to inhibit paresthesia.

Another aspect of the invention is a method for stimulating the spinal cord of a subject so as to inhibit pain transmission. The method comprises applying through a plurality of electrodes directly in contact with the spinal cord an electrical stimulus so as to render sensory neurons within the spinal cord refractory to transmission of synchronous action potentials initiated within the spinal cord.

Another aspect of the invention is a device for stimulating the spinal cord of a subject so as inhibit pain transmission. The device can comprise the following components: (a) a compliant backing configured to conform to a region of the spinal cord within the dura; (b) a plurality of electrodes arrayed along the inner surface of the backing; and (c) circuitry for delivering an electrical stimulus to the spinal cord through the plurality of electrodes, thereby rendering sensory neurons within the spinal cord refractory to transmission of synchronous action potentials initiated within the spinal cord.

Another aspect of the invention is a system for stimulating the spinal cord of a subject so as to inhibit pain transmission. The system can comprises the following components: (a) an implantable signal receiver configured to conform to a surface of a region of the spinal cord, the transceiver having a plurality of contacts configured for electrical coupling to corresponding positions in said region; and (b) a signal generator comprising a microprocessor programmed to generate an electrical stimulation signal. The receiver can be configured to receive said signal from the signal generator, and to transmit the signal to the corresponding positions in said region of the spinal cord. This can render sensory neurons within the spinal cord refractory to transmission of synchronous action potentials initiated within the spinal cord.

Another aspect of the invention is a system for stimulating the spinal cord of a subject who is prone to deleterious nerve signals transmitted along the spinal cord. The system can comprise the following components: (a) an electrical stimulation device including a compliant backing configured to conform to a region of the spinal cord, and an electrical stimulation surface disposed within an inner surface of the backing, the electrical stimulation device configured to be implanted within dura of the subject so that the stimulation engages the spinal cord; and (b) a signal generator coupled to the electrical stimulation surface. The generator may be microprocessor controlled, and is configured and programmed to apply an electrical stimulus from the electrical stimulation surface directly to the spinal cord with a sufficiently high frequency to inhibit manifest stimulation-induced paresthesia.

In any of these methods, devices, or systems, the electrical stimulus is intended to promote stochastic depolarization of sensory neurons within the spinal cord. It may have a potential that alternates at high frequency, such as 1,000 to 9,000 Hertz. The electrical stimulus can have a potential that varies according to a non-uniform pattern, or that varies at stochastic intervals. It can be administered to the spinal cord through an array of 10 or more electrodes in direct contact with the spinal cord. The device can be configured so that different stimuli are conveyed through different electrodes in the array.

A device or system of this invention may also have a means for monitoring transmission of synchronous action potential through the spinal cord, and a means for adjusting the electrical stimulus so as to further inhibit transmission through the spinal cord of synchronous action potentials. Thus, the user may monitor transmission of synchronous action potential through the spinal cord, and adjust he electrical stimulus so as to further inhibit transmission through the spinal cord of synchronous action potentials. The stimulus can be applied so as to inhibit sensation of pain, or to inhibit symptoms of Parkinson's disease, spinal cord injury, or congestive heart failure.

Other aspects of the invention will be apparent from the description that follows.

DRAWINGS

Figure 3A:
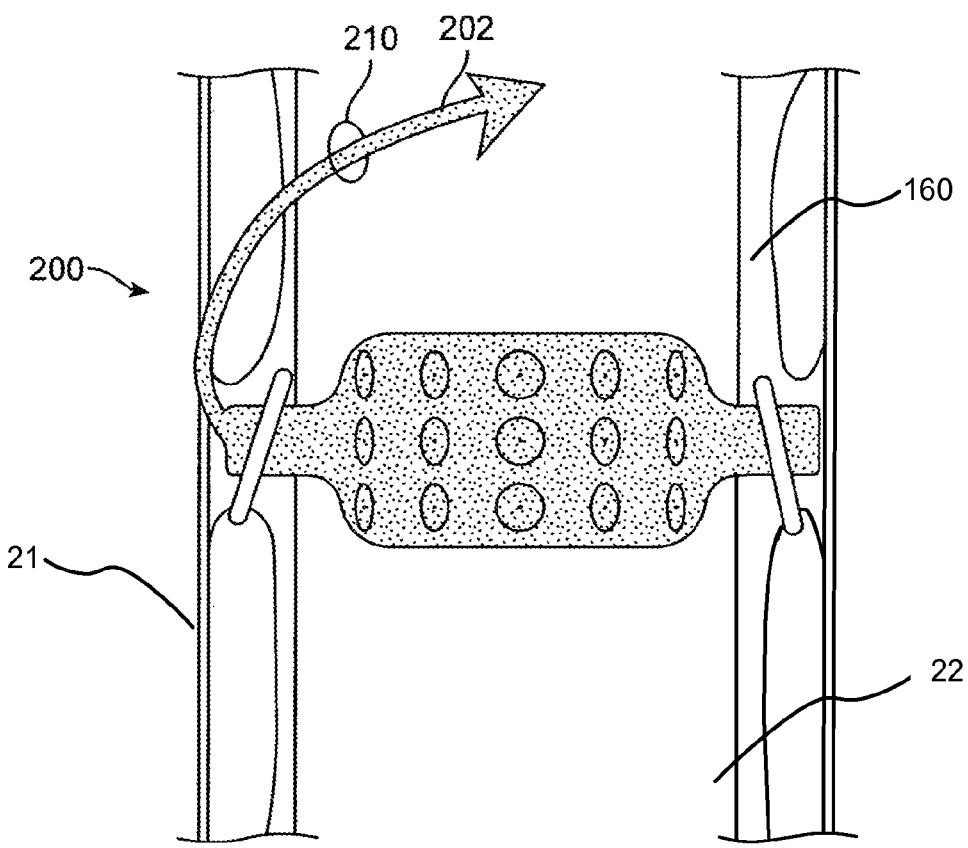

FIGS. 3(A) and (B) depict an electrode array implanted onto a spinal cord. Lead 202 passes out of the spinal canal to bring power and control signals to the array.

Figure 4A:
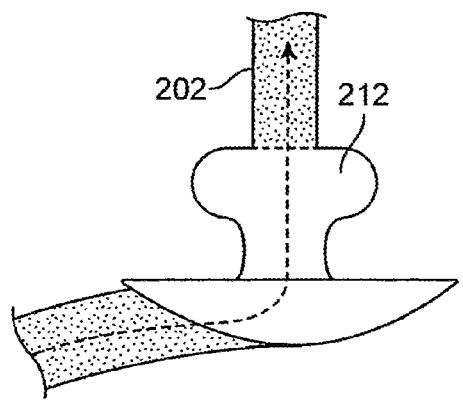
Figure 4B:
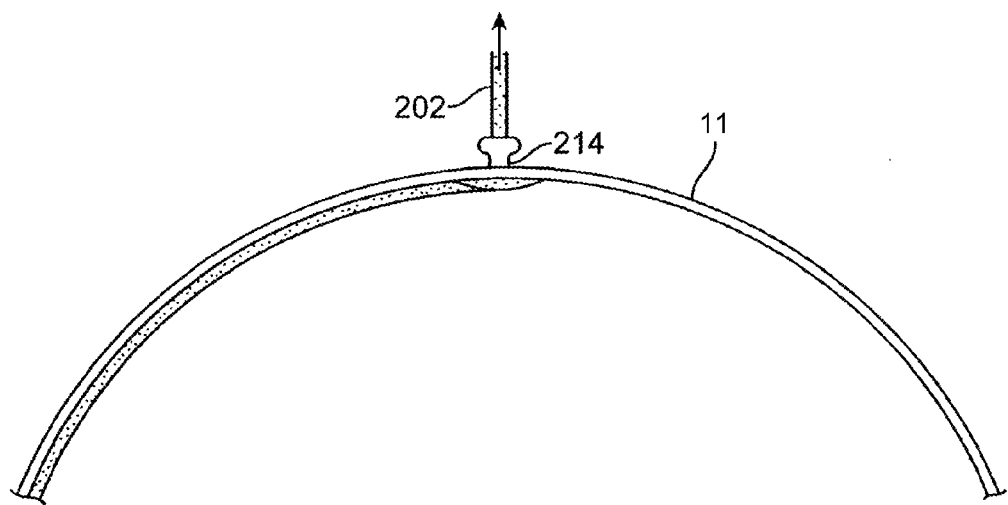
Figure 4C:
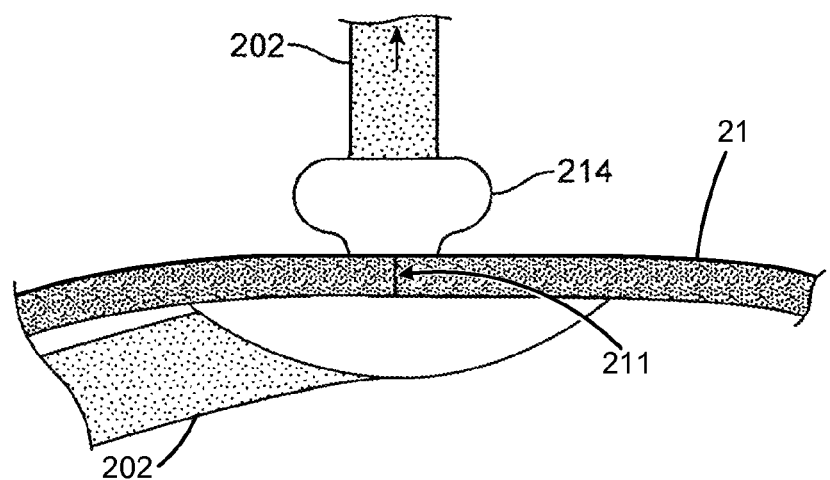
Figure 4D:
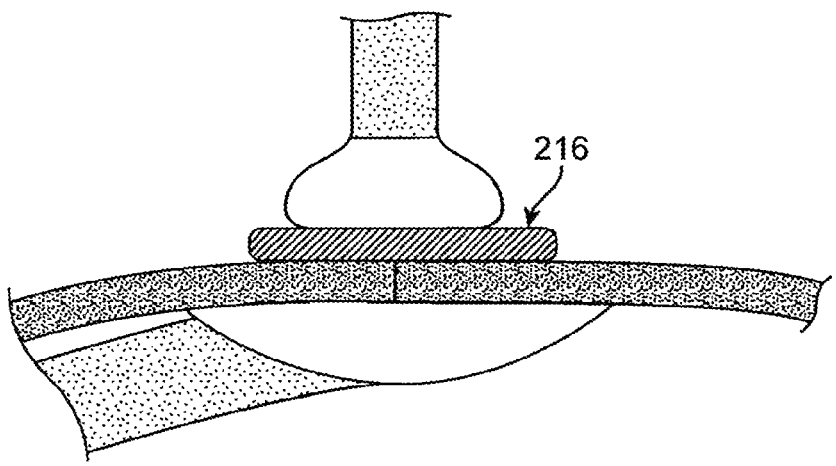
Figure 4E:
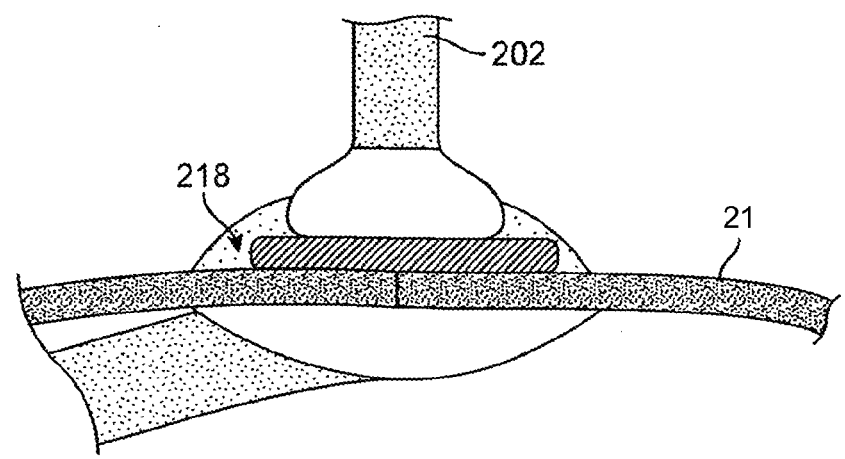

FIGS. 4(A) and (B) show details where the lead is adapted to pass through the dura. FIGS. 4(C), (D), and (E) show the fitting being installed and glued into place to prevent leakage across the dura.

Figure 5:
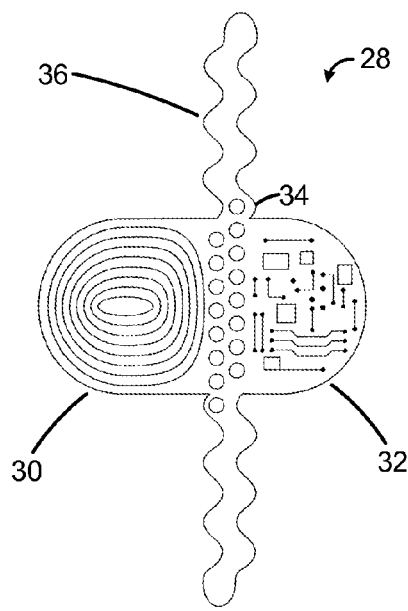

FIG. 5 shows an electrode array that has been adapted to receive power and control signals wirelessly.

Figure 6:
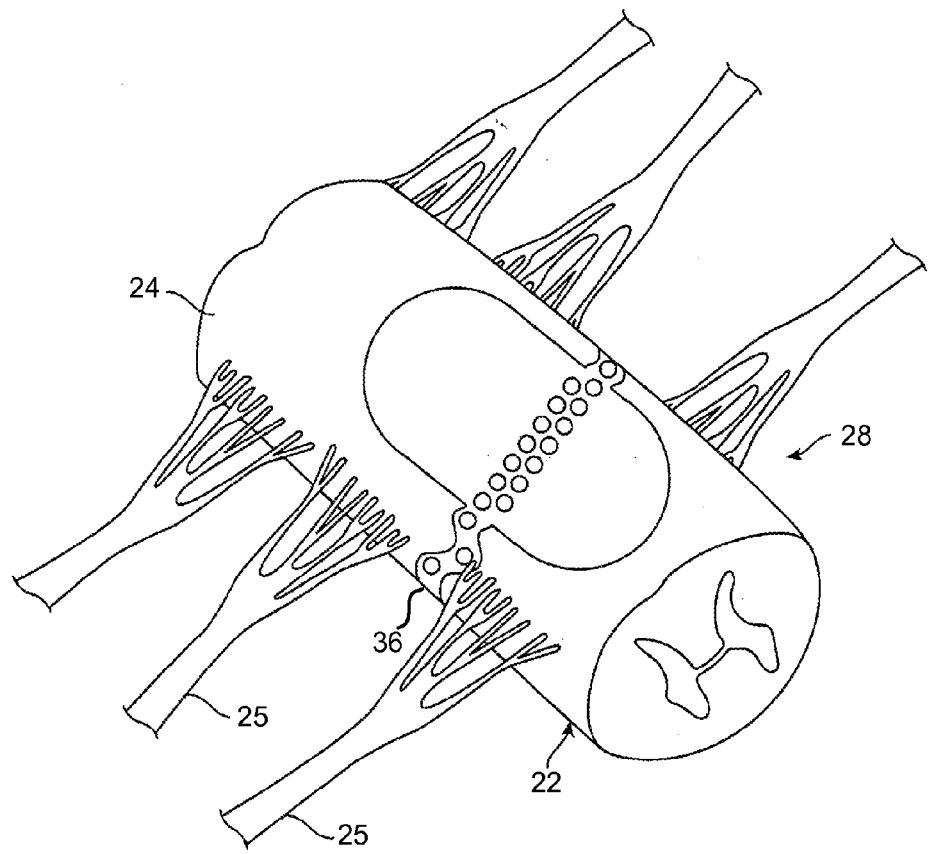

FIG. 6 is an oblique view of the wireless array implanted onto the spinal cord.

Figure 7:
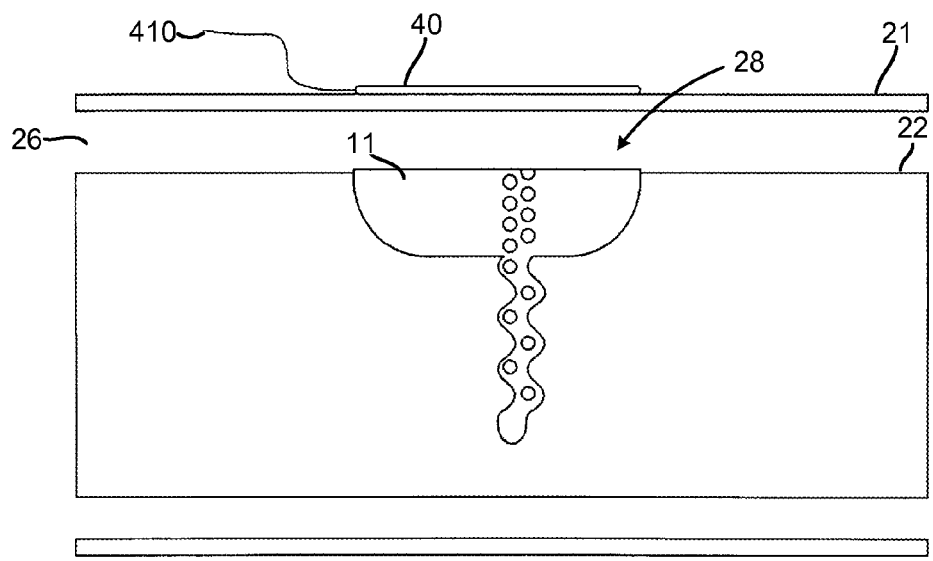

FIG. 7 is a transverse view of the array after implantation, with the dura cut away.

Figure 8:
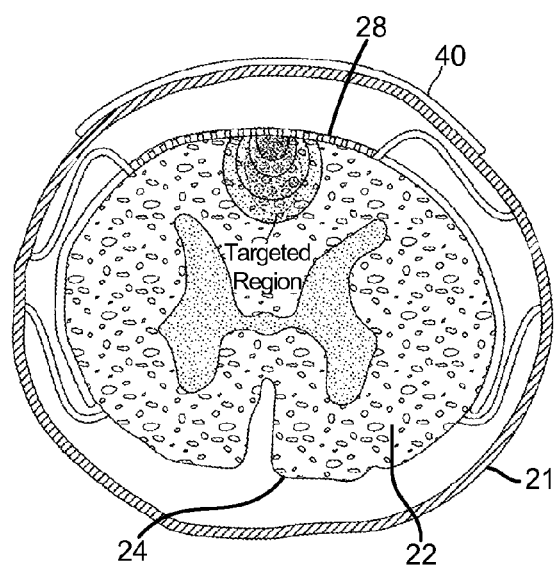

FIG. 8 is a longitudinal cross-section of the spinal cord with the implanted array. The shaded rings represent electrical stimuli coming downward from the array to the region targeted for treatment.

Figure 9:
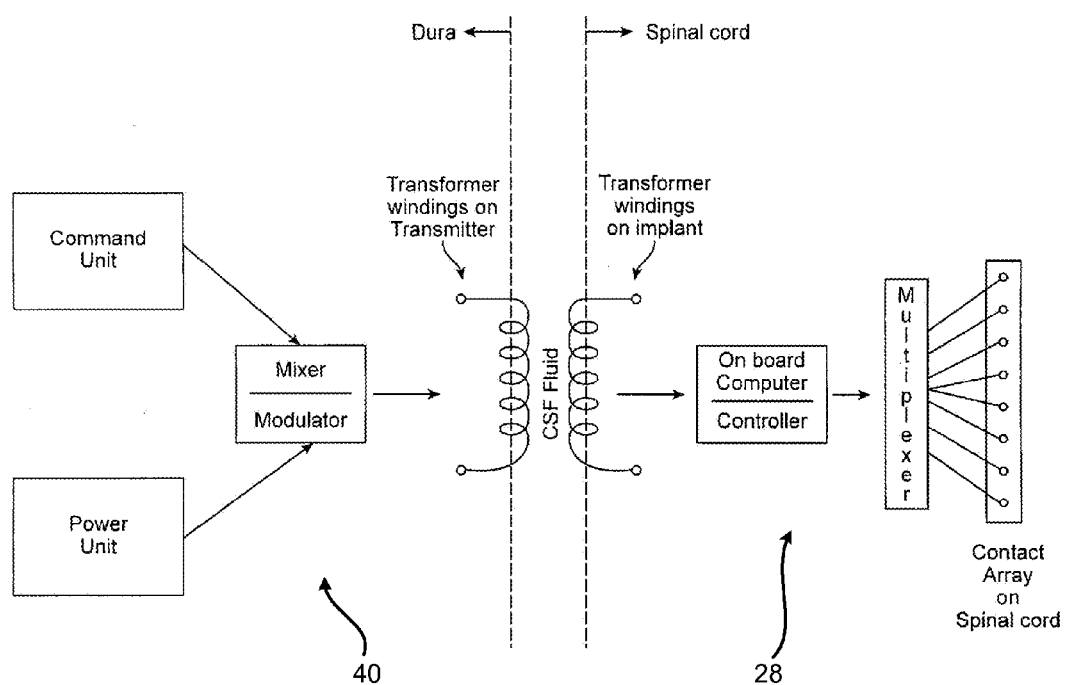

FIG. 9 is a schematic representation of the inductive coupling between the transmitter providing power and control signals, and the receiver coils adjacent to the electrode array.

Figure 10A:
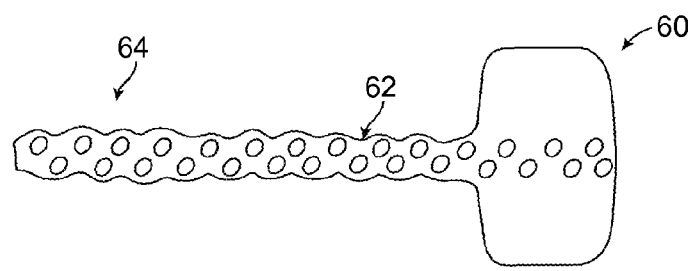

FIGS. 10(A) and (B) show an electrode array configured for attachment to the spinal cord in a wrap-around configuration.

Figure 11:
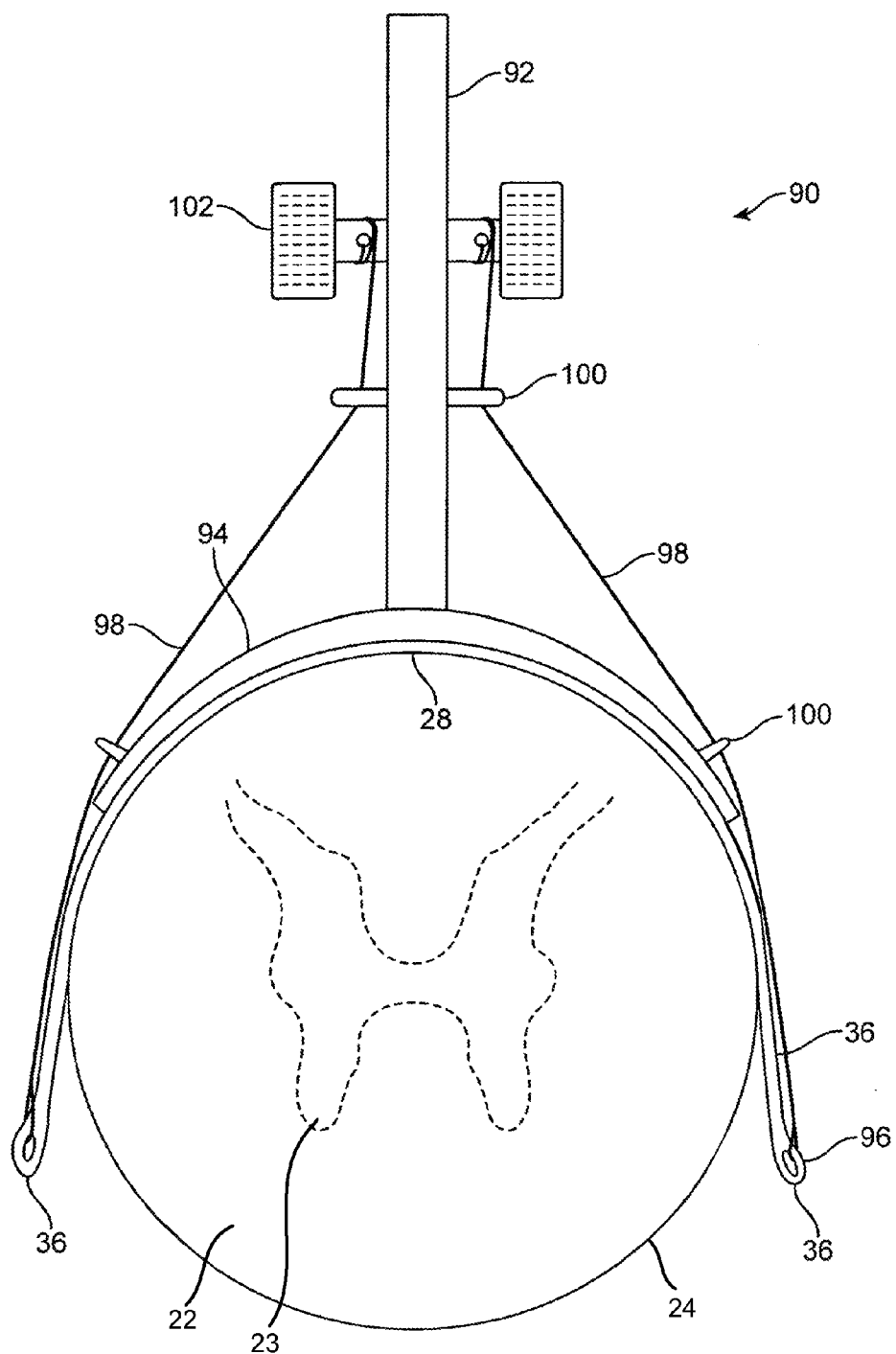

FIG. 11 illustrates a device that can be used by the neurosurgeon to implant the wrap-around electronic array into a spinal cord.

Figure 12:
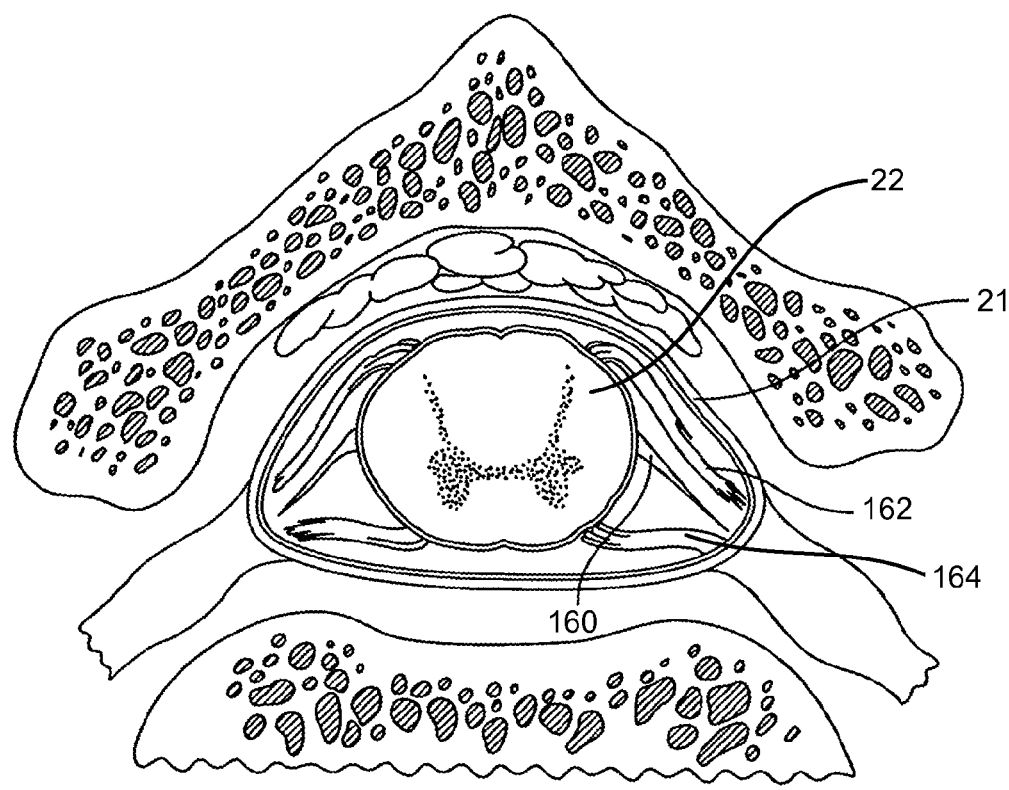

FIG. 12 represents a cross-sectional view of the human spinal cord and surrounding tissue.

Figure 13:
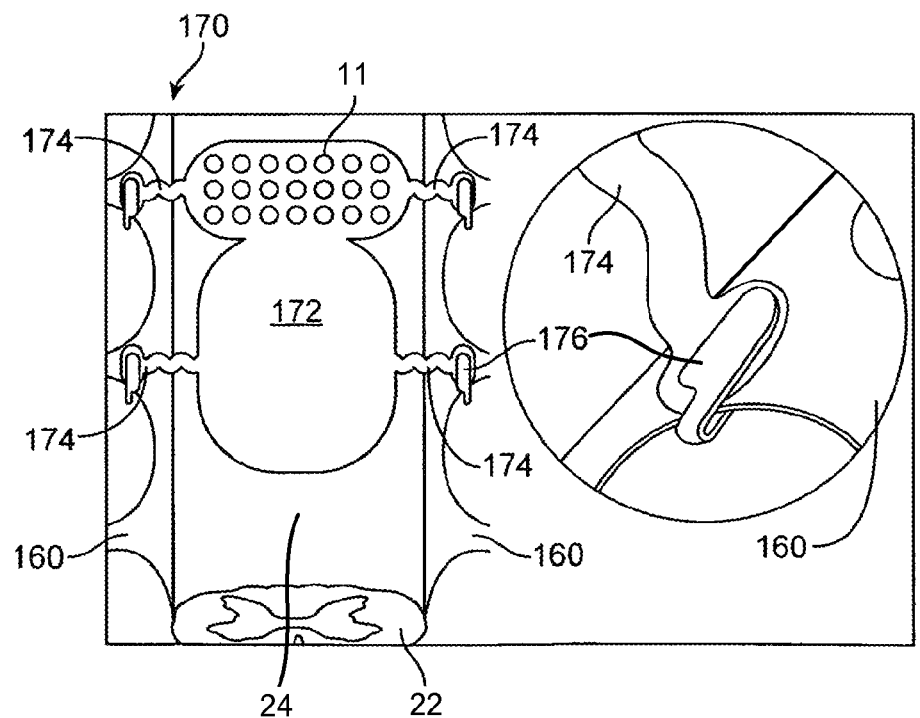

FIG. 13 shows an electrode array configured to be clamped to the dentate ligament on each side of the spinal cord. The inset shows a detail of a clip that affixes an extension of the array to the ligament.

Figure 14A:
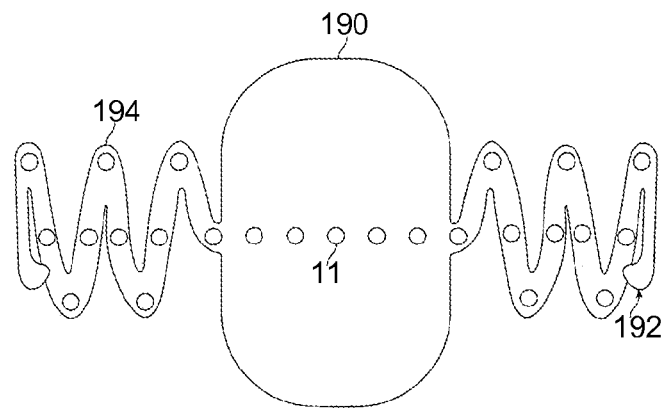

FIGS. 14(A) and (B) show another electrode array configured for attachment to the dentate ligament. In this case, the clasp or tab for affixing the array is a further extension of the array's backing material.

DETAILED DESCRIPTION

This invention provides a new technology for management of back pain, leg pain, and other conditions by stimulating the spinal cord in a manner that renders it refractory to transmission of deleterious or undesirable sensory input. The electrical stimulus comprises high frequency pulses in a regular or complex pattern or that are stochastically produced under microprocessor control. The stimulus is applied directly to the surface of the spinal cord from within the spinal canal, which provides important benefits over previous technology. The stimulus alleviates symptoms and signs of back pain, while inhibiting or minimizing the risk of side effects such as paresthesia, and potentially minimizing any side effects on essential neurological processes such as motor neuron transmission and proprioception.

Rationale

This section discusses certain neurophysiological phenomena that may underlie some of the benefits of this invention. The discussion is provided for the benefit of the reader and to help advance the art. It should not be interpreted as imposing any limits on the practice of the invention. The reader may implement and advance the devices and methods of this invention without understanding or proving any of the phenomena propounded here.

High frequency stimulation of the spinal cord may benefit the patent by inducing a state of pseudospontaneous axon firing. Bundles of sensory axons are thought to fire randomly when not transmitting sensory stimulus. When a sensory stimulus is presented, a substantial proportion of the axons within a bundle or pathway will discharge in a synchronous fashion—firing axons potentials at about the same time. This results in the sensory input being transmitted along the axons in the bundle, so that the subject may experience the sensation. Stated differently, the absence of sensation is coded by random timing of axon firing within a bundle, whereas a sensory perception is coded by synchronous firing of a population of axons.

It is a hypothesis of this invention that patients with leg and back pain have bundles of axons spontaneously firing in a synchronous manner (or some other non-random fashion), instead of the normal random pattern of firing. Electrical pulses will entrain axonal firing. A single pulse delivered to a bundle of axons will cause them all to fire synchronously. If the time interval between each electrical shock in a pulse train is longer than the refractory period of the axons in the bundle, each subsequent shock will also synchronously activate all of the axons, and a subject will experience a sensation. A low frequency alternating current applied to the back (50 Hz) may be effective in reducing the sensation of pain, but the stimulation may generate neurological side effects such as paresthesias (tingling or numbness).

A high frequency electrical stimulus (say, about 5,000 Hz) has interval spacing shorter than the refractory period of axons. An individual axon cannot fire again in response to a second shock until its membrane potential has recovered from the effects of the first shock, and this takes time. Different axons have different refractory periods. By delivering electrical pulses at high frequency, the relative timing of firing by individual axons within the bundle of axons becomes nearly random, with different axons become excitable again at different times. Applying high frequency pulses to the spinal cord can be used to restore a state of active quiescence in the sensory nerves passing through the cord.

"Quiescence" as the term is used in this disclosure in reference to a bundle of axons refers to a condition of stochastic depolarization or firing of axons within the bundle. It is a natural condition in which the neurological system may be actively signaling that there is no sensory input to be transmitted by the bundle as a whole. It may be induced by pseudospontaneous neural stimulation by applying effective high-frequency electrical pulse patterns in an appropriate manner as described here.

Benefits

This invention provides a new technology whereby high frequency electrical stimulus is applied directly to the spinal cord. It represents an important advance in the management of back pain, because targeted axons can be subject to an electrical stimulus without exposing the dorsal rootlets to suprathreshold levels of current.

Besides providing the clinician with new modalities for pain management, attributes of the technology include the following:

1) Low Power Consumption.

Because the devices of this invention delivers stimuli directly to the spinal cord, the power consumption is lower compared with devices used to treat back pain from outside the spinal canal. The power required by a device of this invention may be as low as 30%, 10%, or even 5% or less of what is required by a standard extra-dural electrode. In some embodiments, devices of this invention implanted with a battery power source may provide pain relief for several days, often for a week or much more.

2) Variable Waveforms and Frequencies.

Because of the effects of cerebrospinal fluid (CSF) and other soft tissues, a high frequency square waveform delivered through these tissues will be significantly attenuated and distorted by the time the electrical pulses reach the spinal cord. The pulses reaching the spinal cord will have a different spectral composition, i.e., be a different waveform with potentially different frequency components. Electrical stimulation from the devices of this invention should not be distorted and attenuated to this extent, because there is no intervening fluid or tissue between the stimulating electrode and the targeted axons. Varying the amplitude of the pulses according to a complex pattern or in a stochastic fashion may be more effective when delivered directly to the spinal cord.

3) Penetration into the Spinal Cord.

A direct contact electrode array according to this invention may allow the user to apply stimulation much deeper into the spinal cord (more than 0.5 or 1.0 mm below the surface). This compares with standard extra-dural electrodes, which may be effectively limited to altering signal transmission adjacent the spinal cord surface adjacent the anterior dura. As nerve signals may be transmitted, at least in part, by neurons at a range of depths, this may facilitate treatment of conditions that are less amenable to treatment using other technology.

4) Spatially Selective Stimulation.

Normal spinal cord signaling is essential to allow a subject to sense the ground and move their legs. The neural pathways required involve populations of axons that fire synchronously. For this reason, if an electrical stimulus interfered indiscriminately with the coordination of action potentials within the spinal cord (for example, delivering the stimulus epidurally), the treated subjects may have deficits in proprioception and kinesthesia. This in turn may cause stumbling or gait abnormalities. The technology of this invention helps avoid this problem by more precisely targeting the neurological pathways that transmit the sensation of pain. Specifically, the device is deployed on the lateral surface of the spinal cord, and so is proximal to white matter of the spinal cord. In addition, the electrode arrays can be placed strategically to maximize any trade-off between pain relief and interference with neural pathways transmitting essential information.

Particular Features of the Invention

This invention generally provides a method for stimulating a spinal cord of a subject, such as may be clinically desirable in pain management or the treatment of several other medical conditions. The patient is prone or susceptible to deleterious nerve signals transmitted along the spinal cord, or otherwise requires treatment. An electrode array is implanted within the spinal canal so that the electrodes engage the spinal cord. An electrical stimulus is through the electrodes in the array directly to the spinal cord so as to inhibit transmission of the deleterious nerve signals along the spinal cord. The electrical stimulus has a sufficiently high frequency to inhibit sensory side effects such as paresthesia (numbness or tingling).

Put another way, the spinal cord is stimulated so as to inhibit pain transmission by applying directly to the spinal cord an electrical stimulus that renders sensory neurons refractory to transmission of synchronous action potentials initiated within the spinal cord. This inhibits back pain from locally induced sensory input, and side effects such as paresthesia that may be induced in the course of local treatment. The electrical stimulus is thought to promote stochastic depolarization of sensory neurons within the spinal cord, thus inducing a state of neural quiescence.

To accomplish this, the electrical stimulus comprises a potential that alternates at high frequency. Regardless of the way the potential may vary over time, the frequency may be calculated by determining the number of positive-to-negative alterations per unit time. Effective frequency ranges depend on place of placement of the electrode array, the features of the array, the nature and health of the tissue where the array is placed, and the objectives of treatment. The general object is to induce refractoriness of the spinal cord to transmit deleterious signals or synchronous depolarization events initiated locally. This can be adjusted empirically by determining neural activity and recording the symptoms experienced by the patient.

Depending on the objective of the treatment and the manner in which the technology is deployed, effective pulse repetition rates or frequencies may be at or above 100 Hz (pulses per second), 200 Hz, 500 Hz, 2,000 Hz, or 5,000 Hz, a frequency of about 1,000 Hz, 4,000 Hz, or 10,000 Hz, or a frequency range of about 500 to 50,000 Hz, 1,000 to 9,000 Hz, 3,000 to 8,000 Hz, 2,000 to 20,000 Hz, or 5,000 to 15,000 Hz.

The electrical potential may vary at a regular frequency in a sinusoidal or square wave form. Alternatively, the wave form may be a more complex pattern, with pulses appearing at varying intervals and intensities according to a calculated or repetitive pattern. Such patterns comprise a pulse train generating substantially continuous activation of nerves within the spinal cord, and may incorporate irregular pulse intervals, irregular pulse amplitudes, a variety of wave forms (for example, monophasic, biphasic, rectangular, sinusoidal, as well as asymmetric or irregular wave forms), or any combination thereof. The potential may create what is essentially a broad band noise, varying at stochastic or essentially random intervals and intensity under the influence of a suitable computational algorithm or automated control program in a microprocessor.

Further information on pseudospontaneous neural stimulation is described in U.S. Pat. Nos. 6,295,472 and 6,631,295, and J T Rubenstein et al., Hearing Res. 127(1), 108-118, 1999, which are hereby incorporated herein by reference in their entirety for all purposes.

The electrodes through which the high-frequency stimulus is conveyed are typically arrayed on a pliable background, constructed of a material and in a shape that allows it to be conformed directly to the spinal cord. The plurality of electrodes may comprise at least 10, at least 20, at least 30, or at least 50 electrodes. They may be arrayed on the backing in a grid, a rectilinear pattern, or any other arrangement that is effective. Optionally, the technology may be configured to apply different stimuli through different electrodes in the array.

Treating back pain according to the invention may comprise administering an effective electronic stimulus to the spinal cord, monitoring transmission of synchronous action potential through the spinal cord, and then adjusting the electrical stimulus so as to further inhibit transmission through the spinal cord of synchronous action potentials. The object may be anything that is clinically worthwhile, such as reducing sensation of pain (especially back pain) by the subject, such as may occur in the course of spinal cord injury, disease or strain of the spinal cord, Parkinson's disease, osteoarthritis, or congestive heart failure.

The electrical stimulus may be adjusted in frequency or other waveform parameters, and manner of application so as to minimize side effects such as paresthesia, and to minimize impact on transmission of essential neurological faction, including motor neuron activity, and nerves involved in proprioception and kinesthesia. Optionally, the clinician or the user may be provided with an input means to select the pattern, adjust the frequency, and adjust the intensity in accordance with the perceived symptoms.

The devices and systems of the invention also have circuitry configured to deliver an electrical stimulus to the spinal cord through electrodes. The circuitry may be built into the same backing as the electrodes. Power and control signals can be provided to the circuitry and the electrodes by electrical leads that pass out though the dura. Alternatively, the device may have a receiving means such as an antenna through which to receive power and control signals wirelessly from an external source. A "one size fits all" design is desirable, whereby a standard device can accommodate almost the full range of spinal cord anatomy variants encountered in patients. When this is not practicable, the electrode array and the features for securing on or about the spinal cord can be built in different sizes to suit different patients.

Technology Platform

The invention described here incorporates features that are also described in WO 2012/065125. That application provides devices for direct spinal cord stimulation that are remotely controlled and laterally supported. For the electrode array to be implanted in the spinal cord for use on an ongoing basis, the device is secured so that it maintains direct contact with the desired region of the spinal cord.

The technology platform provides an advance over previous devices and methods in pain management in a number of respects. Included are the following:
- a dense array of electrode contacts delivers highly localized, spatio-temporally synchronized, and positionally selective electrical stimuli to any targeted region of the spinal cord;
- the implantable electrode assembly has an ultra-thin physical profile that does not obstruct or alter flow patterns of cerebrospinal fluid (CSF) around the spinal cord;
- the contact forces between the device and the spinal cord are stable and unvarying, and hence patient movement does not affect these contact properties, which results in optimal electrical coupling between electrode contacts and spinal cord tissue;
- the compliant nature of the device materials accommodates pulsations of the spinal cord without any harmful reactive or dissipative counter-forces;
- the surgical procedure used to implant the device is well established and safe, and when performed by skilled practitioners, the risk of CSF fistula formation with this procedure is minimal, and can potentially be done in 30 minutes;
- manufacture of the device is uncomplicated and cost-effective.

Aspects of this technology are illustrated in FIGS. 1 to 14, and described below.

Figure 1:
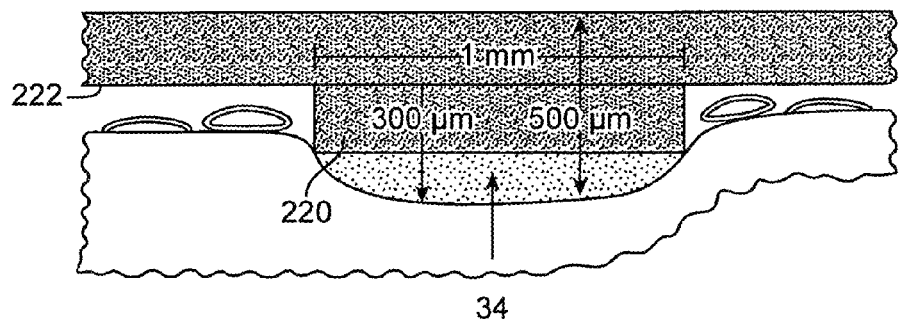
FIG. 1 is a schematic depiction of an electrode in cross-section, extending from the backing upon which it is arrayed.

FIG. 1 schematically illustrates an electrode projecting from an interior surface of a backing or substrate. Therapeutic benefit may be enhanced by maximizing current densities in the targeted conducting tracts of the spinal cord itself, while minimizing the current density shunted away by the CSF. The electrodes are engaged against the surface of the spinal cord as shown, with a stand-off column 220 extending between the exposed portion of the electrode 34 and the underside of the implant substrate body 222. This can support the implant off the surface of the spinal cord by about 100 µm to accommodate pulsation of the spinal cord 22. By insulating the surface of stand-off column 220, it is possible to minimize the shunting effect of the CSF, since the exposed portion of the electrode will be in contact only with the pial surface 24 of the spinal cord, and not with the CSF itself. Gentle inward pressure causes slight inward "dimpling" of the pial surface by the electrode. As a result, the active exposed surface of the electrode is "sealed" by spinal cord tissue enveloping the protruding portion of the contact. A small gap separates the electrically inactive portions of the array, providing space into which the spinal cord tissue may expand and contract with cardiac pulsation cycles.

Figure 2:
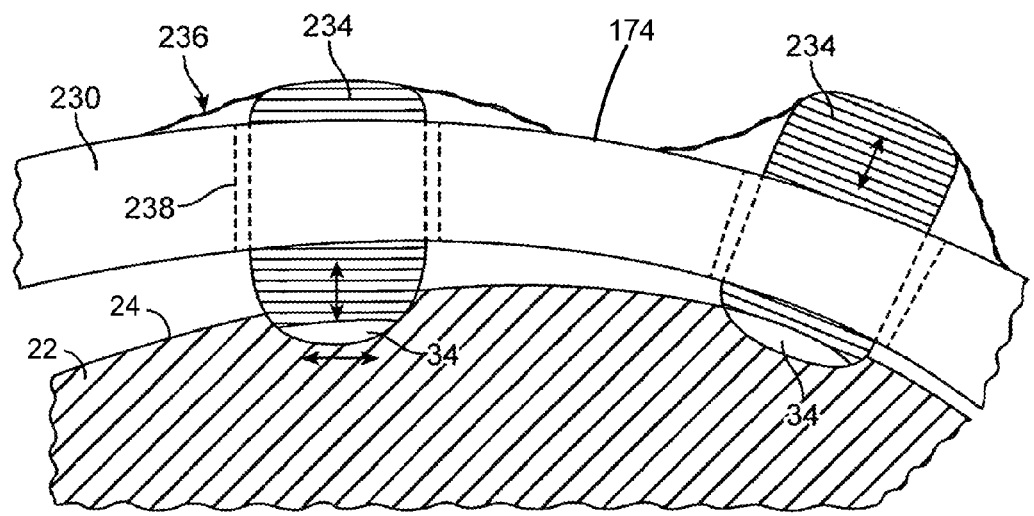
FIG. 2 shows electrodes arrayed in the backing so as to provide a degree of mobility.

FIG. 2 schematically illustrates individual electrodes 34 flexibly mounted to a backing or substrate 230 by a soft resilient material 232 so as to allow the electrode to resiliently float or move radially and/or laterally relative to the substrate by a distance that is at least as large as the pulsations of the surface 24 of spinal column 22. This movement of each electrode may inhibit sliding engagement of the electrodes against the surface of the spinal cord during pulsation. In some implementations, the only parts of the array that directly engage the spinal cord are the electrode contacts. These may serve as mechanical anchoring points for the device. They exert enough pressure to maintain good electrical contact with the surface of the spinal cord. The pressure exerted should be generally even for all of the contacts, for example, by having electrodes protruding slightly from contoured attachments arms 174. This positions all contacts in the desired position in relation to the surface of the spinal cord. Outward and inward movements of the contacts (e.g. with pulsations and respirations) are accommodated by movements of the semi-rigid attachment arms Each contact is mobile and attached to the backing via an elastic or spring-like interface. The degree to which each contact extends out from the attachment arm is determined by the distance separating the attachment arm from the spinal cord surface at each contact location. The elastic nature of the connection between each contact and the attachment arm allows each contact to independently protrude out from the device until the desired tissue contact force interface is achieved. In this way, effective interfaces form between electrode contacts and the spinal cord, even if the arms do not conform perfectly to the shape of the spinal cord.

As shown in the figure, the electrode bodies 234 extend through apertures 238 in substrate 230, with the substrate being pliable and having elasticity appropriate to supporting thin film circuit components. A soft elastomeric material 236 spans the apertures from substrate 230 to the electrode bodies, with the elastomeric material here comprising a sheet of material adhered to the outer surface of the substrate. Alternatively, the electrodes may be supported relative to each other and the substrate with a soft elastomeric material spanning directly between the electrode and walls of the aperture. Alternatively, the resilient material may form column 220. Flexible conductors (not shown) may extend between the substrate and electrode bodies within or outside the elastic material with these conductors optionally being serpentine, having loops, or otherwise configured to accommodate movement of each electrode body relative to the substrate.

Figure 3B:
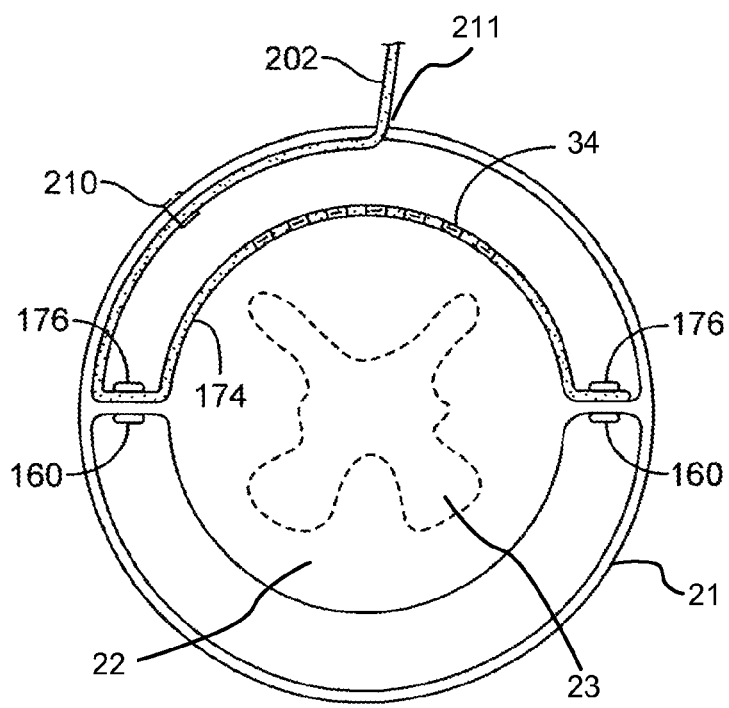

FIGS. 3 and 4 illustrate components of an array device that receives power and control signals from an external source by way of wire leads. A lead extends along and is attached to one of the dentate ligaments and is sealed where it extends through the dura. The device 200 has a flexible lead that extends through dura 21, with the lead preferably extending along one of the ligament attachment arm 174. The lead runs laterally and dorsally, hugging the inner surface of the dura 21, optionally affixed a staple, clip, suture, or stapled bracket 210. The lead 202 may exit the dura 21 along the midline through an incision 211. By placing crimping clips 176 to secure the lead bearing array attachment arm 174 to the dentate ligament 160, strain is relieved, which helps prevent torqueing on the array by the leads, potentially causing injury to the spinal cord A dura-traversing lead fitting 212 can help inhibit lead migration and facilitate water-tight dural closure, with the lead optionally being disposed along a re-approximated mid-line durotomy after closing most of the incision using standard techniques. A compression clip 216 can engage fitting 214 to help seal the dural leaflets to each other around fitting 214, and tissue glue 218 can also be placed on and around the compression clip to effect closure.

FIG. 5 illustrates an array structure element 28 configured to receive power and control signals wirelessly. The turns of a microfabricated coil 30 is configured to serve as a radiofrequency receiver that couples inductively to the counterpart coil on a paired transmitter element, thus allowing the array to receive power, information, and control signals. The circuits 32 constitute the control elements that regulate the size, timing and distribution of the stimuli that act on the electrodes 34. Flexible attachment arms 36 extend from either side of a central body, typically formed at least in part of the substrate or backing material on which circuit components 32 are mounted.

FIG. 6 shows deployment of the receiver device 28 on the surface of the spinal cord. In this case, the extension arms 36 of the receiver device 28 partially encircle the body of the spinal cord, thus gently clamping the device in place. The extension arms are positioned to reside between the dorsal rootlets 25, and not to be in contact with them. Some dorsal rootlets may be sectioned to accommodate placement.

FIG. 7 shows a lateral view of the relative positions of the transmitter 40 and receiver 28 components, on the surfaces of the dura 21 and spinal cord 22, respectively. Electrical leads 410 connect the transmitter 40 to a battery and control box. The transmitter 40 (an extra-dural power and signal transfer circuit membrane) and receiver 28 patches are inductively coupled to each other by electromagnetic fields established through current flows in the windings on their respective surfaces. The strength of the coupling can be adjusted by regulation of the strength of the current flow. In this way, power, information, and control signals can span the zone of CSF 26 resident between the inside surface of the dura and the outer surface of the spinal cord.

FIG. 8 shows a cross-sectional view of the relative positions of the transmitter 40 and receiver 28 devices, on the surface of the dura 21 and surface 24 of the spinal cord 22, respectively. By positioning the array directly on the surface of the spinal cord, it is possible to drive the electrodes such that the stimuli fields penetrate through the whole treatment zone of interest and are not attenuated by the CSF. The stimulus field concentration helps ensure against parasitic excitation of the dorsal rootlets, with the resulting associated pain. To a rough approximation, the instantaneous electric field, E, within the stimulation zone will be given by $E=\sigma/2\kappa\in_0$ where $\sigma$ is the surface charge density created at the electrode's surface, $\kappa\in_0$ is the product of the dielectric constant of the spinal cord substrate and the permittivity of free space. End effects associated with the geometry of each individual stimulus electrode will modify this simple model, as will superposition of the fields due to the simultaneous activation of one or more neighboring electrodes.

FIG. 9 is a schematic representation of the inductive coupling that takes place between the transmitter 40 and receiver 28. The power, information, and control signals generated by the transmitter device on the dura side of the system are inductively coupled across the CSF fluid to the receiver device, where they are operated on by the on-board controller, and stimuli signals are distributed to the electrodes. The inductive coupling is governed by the mutual inductance between the two sets of windings.

To prevent the device from being displaced in the course of pulsing of the spinal cord or day-to-day movement of the subject, it may be secured to the spinal cord or neighboring tissues. This section describes how an electrode array may be secured by extending the backing to wrap around the spinal cord or attach to the dentate ligaments.

Figure 10B:
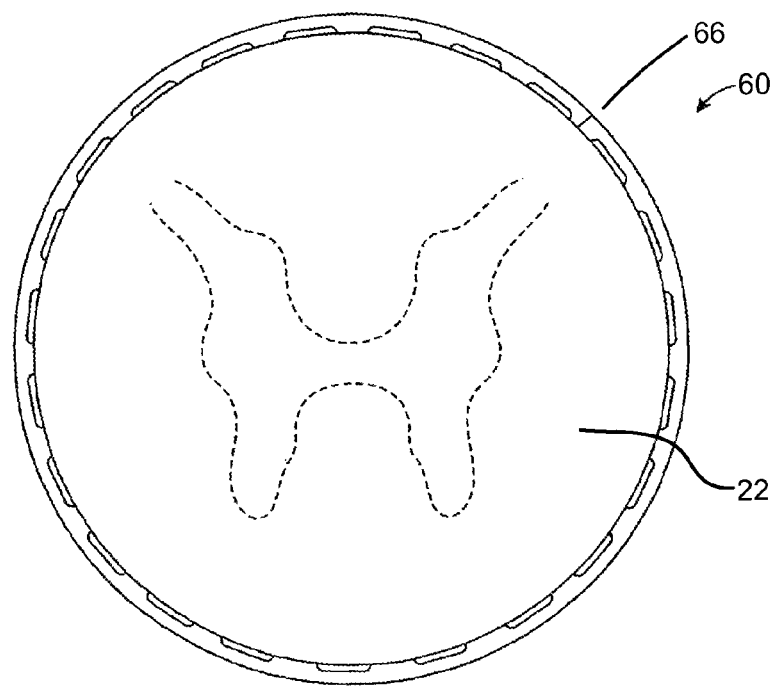

FIG. 10 illustrates an electrode array secured directly to the spinal cord 22 by way of a wrap-around design. A dense array of electrode contacts 62 is imbedded in a flexible band 64 extending from a body of the device and capable of fully circumscribing the spinal cord. This flexible band 64 is inserted in the space between the dura and the spinal cord and gently advanced until the leading edge is visible on the opposite side of the spinal cord. The leading edge of the electrode band is then crimped or pinned at the fusion point 68 or otherwise secured to the main assembly by a crimping device 66. The pliable band positions the electrode contacts in an un-interrupted linear array covering the entire circumference of the spinal cord.

FIG. 11 shows an example of a device used in implantation of an electrode array with extensions that wrap around the spinal cord. It is referred to here under the name "I-Patch Applier 90". The IPA 90 allows the surgeon to maintain a rigid, but reversible attachment to the array main assembly of receiver 28. While maintaining a rigid attachment of the array with a main assembly of the IPA 90, the surgeon may position of the array's pliable attachment arms in an incremental, precisely controlled, and reversible manner. After the array is placed on the spinal cord, and the flexible attachment arms are in their final position, the surgeon can safely and efficiently detach the array from the IPA.

In the IPA 90, a stabilizing plate 94 is attached to the end of rod 92. The plate 94 is contoured to match the curvature of the array device 28, which in turn is contoured to match the curvature of the spinal cord (SC). The array main assembly contains the transceiver antenna and control circuitry and fits snuggly into IPA stabilizing plate 94. The array flexible attachment arms 36 extend away from the main assembly and are contoured to follow the curvature of the spinal cord surface (S). The distal ends of these flexible arms 36 can be reversibly extended during the insertion procedure in order for the array to be placed on the spinal cord. This function is achieved by securing a suture through an eyelet 96 positioned at the termination points of the flexible arms 36.

A double strand suture 98 is then passed through a series of islets 100 until secured to a suture tension adjustment rod having a knob 102. The surgeon rotates this rod to adjust the conformation of the extension arms. When the array is being inserted onto the spinal cord, the adjustment rod is rotated into a position that achieves the desired degree of flexible arm extension. Once the array is in the desired position, the surgeon rotates the adjustment rod until the flexible arms have returned to their pre-formed position, resulting in uniform, gentle, direct contact of the entire array device with the spinal cord surface. The surgeon then disengages the IPA from the array by cutting the tension sutures. The cut sutures are gently removed, followed by removal of the IPA. The entire insertion procedure can be accomplished in about 15 seconds Alternatively or in addition, an electrode array of this invention can be secured to the dentate ligaments. This is effective, since the normal function of the dentate ligaments is to suspend the spinal cord within the spinal canal. This approach stabilizes the array in a manner that does not risk injury to the spinal cord from mechanical tethering.

FIG. 12 is a cross-sectional view of the human spinal cord 22, showing the dentate ligaments 160 extending laterally between the spinal cord and surrounding dura. Dorsal rootlets 162 and ventral rootlets 164 may also extend from spinal column dorsally and ventrally of denticulate ligaments 160, with the dentate ligaments generally attaching the left and right lateral portion of the spinal cord to left and right regions along an internal surface of dura 21. Further details of spinal cord anatomy are provided in D S Nicholas et al.; J. Neurosurg 69:276-282 (1988), and R S Tubbs et al.; J. Neurosurg 94:271-275 (2001).

FIG. 13 shows an electrode array adapted for clamping to the dentate ligaments. The device 170 has an electrode array 11 supported by a body 172 including a flexible substrate or backing, with the array configured to engage a dorsal portion of the spinal cord. Dentate ligament attachment features such as flexible arms 174 extend laterally from left and right sides of body 172, with the arms optionally comprising the same substrate or backing material from which the body is formed. The extensions are configured to be attached to left and right dentate ligaments 160 on either side of the treatment region of the spinal cord to secure the array 11 in engagement with the spinal cord. The attachment arms 174 may be more elastic than the array backing, extending laterally from the electrode array. The attachment arms may flair to a larger width adjacent the ends opposite the array, or may have slightly raised groves or texture at or near these ends to facilitate clipping, crimping, or adhesively bonding the arms to the dentate ligament. The insert shows a detail of the clip 176 used to attach the arms 174 to the dentate ligament 160.

Figure 14B:
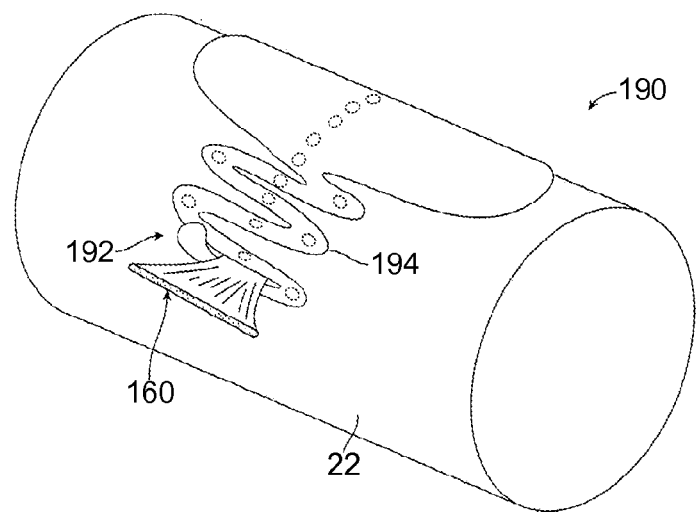

FIGS. 14(A) and 14(B) shows a device 190 that is made entirely with a highly flexible backing so as to avoid restricting normal spinal cord pulsations in situ. There is a simple clasp 192 at the end of each malleable or plastically deformable attachment arm 194. The ends of each attachment arm 194 are secured directly to the dentate ligaments 160.

Use of the Technology

Upon determination that a patient would benefit from electrical stimulation from a device according to the invention, the clinician would first implant the device onto the spinal cord. The location may be predetermined by imaging the spine and/or doing neurological studies, and then selecting a location that would convey the desired benefit. The device is implanted by conforming the arrayed electrodes to a region of the spinal cord so that the electrodes directly contact the spinal cord; and then securing the device in place. Once fixed in place, it remains in contact with the spinal cord after surgical closure, notwithstanding normal pulsation and mobility of the spinal cord, and movement of the patient in ordinary daily activity. The affixing of the device is preferably reversible so that the device can later be removed or repositioned if needed, while causing minimal damage to the tissues.

Where the device comprises extensions configured for attachment to the dentate ligaments, it may be deployed as shown in FIG. 7. The array 170 is placed and centered over the exposed dorsal column of the spinal cord. A small number of rootlets may optionally be sectioned to create room for the attachment arms. The flared end of each attachment arm can be draped on the dentate ligaments on either side of the spinal cord. With the patient in the prone position, gravity results in a gentle fit of the electrode bearing portion of the array on the dorsal spinal cord. The gravitational effect would not occlude surface blood vessels. Microclips 176 or other fixation or crimping devices are used to secure the attachment arms to the dentate ligaments. A broad attachment surface is beneficial, because of the thin, web-like nature of the dentate ligament. The device is simply draped on the dorsal spinal cord surface and dentate ligaments, and affixed in place.

Once the device is in place, it can be used for delivering an electrical stimulus to the target region of the spinal cord. The electrical stimulus typically comprises a pattern of electrical pulses that has been predetermined or is empirically determined to provide the patient with the desired benefit. The stimulus may be applied to inhibit sensation of pain, or to inhibit symptoms or sensory input that is undesirable or disruptive to the patient. This may occur in disease conditions such as Parkinson's disease, spinal cord injury, or congestive heart failure. The stimulus may be provided to the spinal cord by the device on a constitutive basis, in response to feedback data, or it may be subject to the patient's conscious control Each and every publication and patent document cited in this disclosure is hereby is incorporated herein by reference in its entirety for all purposes to the same extent as if each such publication or document was specifically and individually indicated to be incorporated herein by reference.

While the invention has been described with reference to the specific embodiments, changes can be made and equivalents can be substituted to adapt to a particular context or intended use, thereby achieving benefits of the invention without departing from the scope of what is claimed.

The invention claimed is:

1. A method for directly stimulating a spinal cord of a subject, the subject prone to deleterious nerve signals transmitted along the spinal cord, the method comprising:
   (a) securing an electrode array at a position inside the dura of the spinal canal of the subject so that the electrodes directly engage the spinal cord; the array comprising
      (i) a compliant backing configured to conform to a region of the spinal cord within the dura, the backing having an inner surface and an outer surface;
      (ii) a plurality of electrodes arrayed along the inner surface of the backing; and
      (iii) circuitry configured for delivering an electrical stimulus to the spinal cord through the plurality of electrodes; then
   (b) applying an electrical stimulus through the electrodes in the array directly to the spinal cord so that the electrical stimulus inhibits transmission of the deleterious nerve signals along the spinal cord, wherein the electrical stimulus pulses or alternates with sufficiently high frequency to promote stochastic depolarization of sensory neurons within the spinal cord.

2. The method of claim 1, further comprising securing a compliant backing upon which the electrodes are arrayed on or about the spinal cord so that the electrodes are maintained direct contact with a desired region of the spinal cord unaffected by movement of the subject.

3. The method of claim 2, wherein the compliant backing is attached to a dentate ligament.

4. The method of claim 1, wherein the electrical stimulus comprises a potential that varies of a nonuniform pattern.

5. The method of claim 1, wherein the electrical stimulus comprises a potential that varies at stochastic intervals.

6. The method of claim 5, wherein the spinal cord is stimulated by applying different stimuli through different electrodes in the array.

7. The method of claim 1, further comprising monitoring transmission of synchronous action potentials through the spinal cord, and adjusting the electrical stimulus so as to further inhibit transmission through the spinal cord of synchronous action potentials.

8. The method of claim 1, wherein the stimulus is applied so as to inhibit sensation of pain by the subject.

9. The method of claim 1, wherein the stimulus is applied so as to inhibit symptoms of Parkinson's disease, spinal cord injury, or congestive heart failure in the subject.

10. The method of claim 1, wherein the frequency is at least 2,000 Hz.

11. The method of claim 1, wherein the frequency is between 5,000 and 15,000 Hz.

12. A system that is constructed and arranged to stimulate a spinal cord of a subject who is prone to deleterious nerve signals transmitted along the spinal cord, the system comprising:
   (a) an electrode array that includes:
      (i) a compliant backing configured to conform to a region of the spinal cord within the dura, the backing having an inner surface and an outer surface; with
      (ii) a plurality of electrodes arrayed along the inner surface of the backing;
   (b) an array securing component configured to secure the electrode array to the spinal cord or neighboring tissues so that the electrodes remain engaged in position on the spinal cord inside the dura in the course of pulsing of the spinal cord or day-to-day movement of the subject; and
   (c) a signal generator coupled to the electrode array, the generator being configured to energize the electrode array with an electrical potential that pulses or alternates with an average frequency of at least 500 Hz.

13. The system of claim 12, wherein the electrical potential is designed to promote stochastic depolarization of sensory neurons within the spinal cord.

14. The system of claim 12, wherein the electrical potential alternates at a frequency of 1,000 to 9,000 Hz.

15. The system of claim 12, wherein the electrical potential varies at stochastic intervals.

16. The system of claim 12, wherein the array comprises ten or more electrodes configured to convey the electrical stimulus to the spinal cord.

17. The system of claim 12, configured so that different stimuli are conveyed through different electrodes in the array.

18. The system of claim 12, wherein the average frequency is at least 2,000 Hz.

19. The system of claim 12, wherein the average frequency is between 500 and 50,000 Hz.

20. The system of claim 12, wherein the average frequency is between 5,000 and 15,000 Hz.

21. A method for directly stimulating the spinal cord of a subject so as to inhibit pain transmission, the method comprising:
   applying through a plurality of electrodes secured directly in contact with the pial surface of the spinal cord an electrical stimulus that pulses or alternates with an average frequency of at least 500 Hz,
   whereby the electrical stimulus promotes stochastic depolarization of sensory neurons within the spinal cord and inhibits transmission of synchronous action potentials initiated within the spinal cord.

22. The method of claim 21, wherein the average frequency is at least 2,000 Hz.

23. The method of claim 21, wherein the average frequency is between 5,000 and 15,000 Hz.

\* \* \* \* \*